United States Patent [19]

Lesieur et al.

[11] Patent Number: 5,385,944
[45] Date of Patent: Jan. 31, 1995

[54] NAPHTHYLETHYLUREAS AND NAPHTHYLETHYLTHIOUREAS

[75] Inventors: Daniel Lesieur, Gondecourt; Said Yous, Lille; Patrick Depreux, Armentieres; Gérard Adam, Le Mesnil le Roi; Pierre Renard, Versailles; Bruno Pfeiffer, Eaubonne; Béatrice Guardiola-Lemaitre, Neuilly sur Seine, all of France

[73] Assignee: Adir et Compagnie, Courbevoie, France

[21] Appl. No.: 53,911

[22] Filed: Apr. 27, 1993

Related U.S. Application Data

[62] Division of Ser. No. 930,285, Aug. 14, 1992.

[30] Foreign Application Priority Data

Aug. 23, 1991 [FR] France .................. 91 10547

[51] Int. Cl.⁶ .................. A61K 31/17; C07C 335/06
[52] U.S. Cl. .................. 514/585; 564/26; 564/28; 564/48; 564/52; 564/56; 514/595
[58] Field of Search .................. 514/580, 585, 596; 564/17, 26, 28, 48, 56

[56] References Cited

FOREIGN PATENT DOCUMENTS 0344425  3/1988  European Pat. Off. .
1178563  1/1970  United Kingdom .

OTHER PUBLICATIONS

Melatonin and the Pineal Gland–From basic science to Clinical Applications, pp. 303–310, 311–316, 117–122 (1993).
Journal of Endocrinology, vol. 1, No. 1, pp. 1–4 (1989).
Psychopharmacology 100, 222–226 (1990).
Journal of Neurosurgery 63, 321–341 (1985).
Neuropharmacology of Pineal–Secretions 8, Nos. 3–4 247–273 (1990).
Brain Research 528, 170–174 (1990).
Melatonin–Clinical Perspectives, 164–165 (1988).
Science 227, 714–720 (1985).
Clinical Endocrinology 24, 359–364 (1986).

*Primary Examiner*—Shailendra Kumar
*Attorney, Agent, or Firm*—Gordon W. Hueschen

[57] ABSTRACT

A compound selected from those of formula (I):

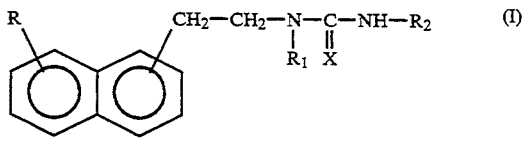

in which the meanings of R, $R_1$, $R_2$ and X are defined in the specification, and medicinal products containing the same which are useful in treating or in preventing a disorder of the melatoninergic system.

13 Claims, No Drawings

NAPHTHYLETHYLUREAS AND NAPHTHYLETHYLTHIOUREAS

The present invention application is a division of our prior-filed copending application Ser. No. 07/930,285, filed Aug. 14, 1992.

The present invention relates to new naphthylethylureas and naphthylethylthioureas, to a process for the preparation thereof, and to pharmaceutical compositions containing them.

Naphthylethylureas having anti-hypercholesterolaemic properties are known from the literature, especially from EP 344 425, which forms the closest prior art.

The Applicant has now found new compounds having the remarkable property of binding intensively and specifically to melatonin receptors.

Those compounds have numerous valuable pharmacological activities on account of their agonistic or antagonistic nature towards melatonin.

In addition to their beneficial action on disturbances of the circadian rhythm and on sleep disorders and seasonal disorders, they have valuable pharmacological properties on the central nervous system, especially anxiolytic, anti-psychotic and analgesic properties, as well as on ovulation, cerebral circulation and immunomodulation.

More specifically, the present invention relates to the compounds of the general formula (I):

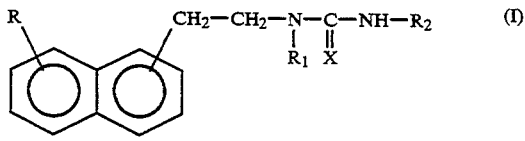

in which:
- R represents a hydrogen atom or a group $OR_3$ wherein $R_3$ represents a hydrogen atom, a straight-chained or branched alkyl radical having from 1 to 6 carbon atoms, a cycloalkyl or cycloalkenyl radical containing from 3 to 8 carbon atoms, an optionally substituted aryl radical, or an optionally substituted arylalkyl or diarylalkyl radical in which the alkyl chain contains from 1 to 6 carbon atoms;
- $R_1$ represents a hydrogen atom or a straight-chained or branched alkyl group containing from 1 to 6 carbon atoms;
- X represents an oxygen or sulphur atom;
- $R_2$ represents a linear or branched lower alkyl radical having from 1 to 6 carbon atoms, an optionally substituted cycloalkyl radical having from 3 to 8 carbon atoms, an optionally substituted ($C_3$-$C_8$)-cycloalkyl-($C_1$-$C_6$)-alkyl radical, an optionally substituted aryl radical, an optionally substituted arylalkyl radical the alkyl chain of which contains from 1 to 6 carbon atoms, or an optionally substituted diarylalkyl radical the alkyl chain of which contains from 1 to 6 carbon atoms, with the proviso that, when R and $R_1$ each represent a hydrogen atom and X represents an oxygen atom, $R_2$ cannot represent a phenyl radical or a 2,6-disubstituted phenyl radical;

the addition salts thereof with a pharmaceutically acceptable base,
the isomers, epimers and diastereoisomers thereof, wherein:
- the term "substituted" associated with the expressions "aryl", "arylalkyl" and "diarylalkyl" indicates that the aromatic nucleus or nuclei may be substituted by one or more groups selected from linear or branched lower alkyl having from 1 to 6 carbon atoms, linear or branched lower alkoxy having from 1 to 6 carbon atoms, hydroxy, halogen, nitro, and trifluoromethyl;
- the term "substituted" associated with the expressions "cycloalkyl" and "cycloalkylalkyl" indicates that the cyclic system may be substituted by one or more groups selected from halogen, linear or branched lower alkyl having from 1 to 6 carbon atoms, and linear or branched lower alkoxy having from 1 to 6 carbon atoms, and
- the expression "aryl group" is understood as meaning a pyridyl, phenyl, naphthyl, thienyl, furyl, pyrimidyl, indolyl, benzofuryl, benzothienyl or quinolyl group.

The present invention relates also to a process for the preparation of the compounds of formula (I), characterised in that an amine of the general formula (II):

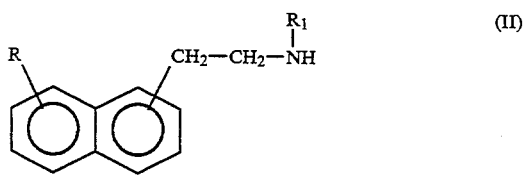

in which R and $R_1$ have the meanings defined above, is treated with an isocyanate or isothiocyanate of formula (III):

in which X and $R_2$ have the same meanings as in formula (I), to obtain the compounds of formula (I),
which compounds of formula (I) may, if desired, be
- purified by one or more purification methods selected from crystallisation, chromatography over a silica column, extraction, filtration, and passage over carbon and/or resin,
- separated, where applicable, in pure form or in the form of a mixture, into their possible optical isomers,
- and/or converted into a salt by means of a pharmaceutically acceptable base.

The compounds of formula (I) have valuable pharmacological properties.

The pharmacological study of the compounds of the invention has in fact shown that they have low toxicity, have significant activities on the central nervous system and, in particular, have sedative, anxiolytic, anti-psychotic and analgesic properties as well as properties on microcirculation, which make it possible to conclude that the products of the invention can be used in the treatment of stress, of anxiety, of seasonal depression, of insomnia and fatigue due to jet lag, of schizophrenia, of panic attacks, of melancholia, of eating disorders, of insomnia, of psychotic disorders, of epilepsy, of Parkinson's disease, of senile dementia, of various disorders associated with normal or pathological ageing, of memory loss, and of Alzheimer's disease, as well as in disorders of cerebral circulation.

In another field of activity, it appears that the compounds of the invention have ovulation-inhibiting and immunomodulatory properties and that they may therefore be used in the treatment of certain cancers and that, when administered externally, they can be used in the treatment of psoriasis, of acne, and of seborrhoea, they protect the skin, and they promote hair growth. They may also be used in veterinary medicine for their properties on the fur.

The present invention relates also to pharmaceutical compositions containing the compounds of formula (I) or, where applicable, an addition salt thereof with a pharmaceutically acceptable base, on their own or in combination with one or more inert, non-toxic, pharmaceutically acceptable excipients or vehicles.

Of the pharmaceutical compositions according to the invention there may be mentioned, by way of non-limiting examples, those which are suitable for oral, parenteral, nasal, per- or trans-cutaneous, rectal, perlingual, ocular or respiratory administration, and especially tablets, dragées, sublingual tablets, sachets, paquets, gelatin capsules, glossettes, lozenges, suppositories, creams, ointments, dermic gels, and injectable and drinkable ampoules.

The dosage varies according to the age and weight of the patient, the mode of administration, and the nature of the therapeutic indication or of any associated treatments, and ranges from 0.1 mg to 1 g per 24 hours.

The following Examples illustrate the invention but do not limit it in any way.

The isocyanates and isothiocyanates of formula (III) are commercial products or can readily be prepared according to processes known to the person skilled in the art, such as the action of phosgene or of thiophosgene on the corresponding primary amines. The amines of formula (II) can be prepared according to the process described in the following preparations, or according to an equivalent process.

PREPARATION 1

2-(7-methoxynaphth-1-yl)ethylamine

STEP A ethyl (7-methoxy-1,2,3,4-tetrahydro-1-naphthylidene)acetate 50 g of 7-methoxytetralone, 40 g of ethyl bromoacetate and 150 cm$^3$ of benzene are mixed by means of a dropping funnel. The mixture is added to activated zinc in the form of needles (18.6 g) according to Reformatsky, and one iodine crystal. The mixture is heated to 60° C. and then refluxed for 45 minutes.

The mixture is hydrolysed on ice in the presence of hydrochloric acid. It is extracted with benzene, dried, and boiled in the presence of P$_2$O$_5$. The product is filtered and dried.

The residue is used as such in the following step.
Yield: 80%

STEP B ethyl (7-methoxynaphth-1-yl)acetate 50 g of ethyl 7-methoxy-1,2,3,4-tetrahydro-1-naphthylideneacetate are mixed with 7.35 g of sulphur, and the mixture is heated at 215° C. for 10 hours. It is cooled, 300 cm$^3$ of ethyl acetate are added, and the mixture is stirred for 30 minutes and filtered. It is then dried.

The resulting residue is used as such for the hydrolysis step.
Yield: 70%

STEP C (7-methoxynaphth-1-yl)acetic acid

A mixture of the ethyl 7-methoxynaphth-1-ylacetate obtained above in 250 cm$^3$ of 20% sodium hydroxide in ethanol is refluxed for 3 hours.

The mixture is dried, and the residue is washed with ether. The product is precipitated with a stream of gaseous hydrochloric acid.

Melting point: 155°–156° C. Yield: 68%

STEP D (7-methoxynaphth-1-yl)acetyl chloride

The 7-methoxynaphth-1-ylacetic acid obtained above is dissolved, while warm, in 300 cm$^3$ of chloroform. The mixture is heated to reflux, and then thionyl chloride is added dropwise. The mixture is refluxed for two hours and evaporated to dryness, yielding an oil which crystallises by cooling. The resulting residue is used as such in the following step.

STEP E (7-methoxynaphth-1-yl)acetamide

The (7-methoxynaphth-1-yl)acetyl chloride obtained above is dissolved in 200 cm$^3$ of anhydrous ether. After cooling the solution with the aid of an ice-salt bath, 200 cm$^3$ of an aqueous concentrated ammonia solution are added, with stirring. The mixture is stirred for 30 minutes, and the resulting precipitate is suction filtered. The product is recrystallised in ethanol.

Yield: 95% Melting point: 201°–202° C.

STEP F (7-methoxynaphth-1-yl)acetonitrile

The (7-methoxynaphth-1-yl)acetamide obtained in step E is suspended in 80 cm$^3$ of anhydrous tetrahydrofuran. Triethylamine is added. The solution is cooled in an ice bath, and then trifluoroacetic anhydride is added dropwise, with magnetic stirring.

The mixture is stirred for one hour at room temperature. It is dried. The residue is taken up in water. The resulting precipitate is suction filtered, dried and recrystallised in diisopropyl ether.

Yield: 83% Melting point : 82°–84° C. Spectral characteristics: Infra-red: 2240 cm$^{-1}$ CN

STEP G 2-(7-methoxynaphth-1-yl)ethylamine

A solution of (7-methoxynaphth-1-yl)acetonitrile in ethanol saturated with ammonia is placed in an autoclave. Raney nickel and hydrogen are added under 300 atmospheres.

The mixture is stirred at 60° C. for one night. It is filtered, and the filtrate is evaporated in vacuo. The resulting oil is used as such as a starting material.

PREPARATION 2

N-methyl-N-[2-(7-methoxynaphth-1-yl)ethyl]amine

Following the procedure of Preparation 1 but replacing ammonia in step E with methylamine, there is obtained N-methyl-(7-methoxynaphth-1-yl)acetamide, which is hydrogenated to form the title compound with borane-dimethyl sulphide in tetrahydrofuran.

PREPARATION 3

2-(6-methoxynaphth-1-yl)ethylamine

Following the procedure of Preparation 1 but replacing 7-methoxytetralone in step A with 6-methoxytetralone, the title compound is obtained.

PREPARATION 4

2-(5-methoxynaphth-1-yl)ethylamine

Following the procedure of Preparation 1 but replacing 7-methoxytetralone in step A with 5-methoxytetralone, the title compound is obtained.

PREPARATION 5

2-(7-methoxynaphth-1-yl)ethylamine

Following the procedure of Preparation 1 but replacing 7-methoxy-1-tetralone in step A with 7-methoxy-2-tetralone, the title compound is obtained.

PREPARATION 6

2-(6-methoxynaphth-1-yl)ethylamine

Following the procedure of Preparation 1 but replacing 7-methoxy-1-tetralone in step A with 6-methoxy-2-tetralone, the title compound is obtained.

EXAMPLE 1

N-[2-(7-methoxynaphth-1-yl)ethyl]-N'-propylurea 0.011 mol of propyl isocyanate is added dropwise, with magnetic stirring, to a suspension of 0.01 mol of 2-(7-methoxynaphth-1-yl)ethylamine hydrochloride in 5 cm$^3$ of pyridine. The mixture is stirred for one hour at a temperature of 80° C., and then the reaction medium is poured onto ice-water. The mixture is acidified with a 1N hydrochloric acid solution. The resulting precipitate is suction filtered, washed with water, dried and then recrystallised in a toluene/cyclohexane mixture.

The title compound is obtained in a yield of 93%.

Melting point: 104°–105° C. Infra-red spectral characteristics: 3300 cm$^{-1}$: v NH (urea) 3040–2820 cm$^{-1}$: v CH (alkyls) 1620–1600 cm$^{-1}$: v CC (aromatic)

EXAMPLE 2

N-[2-(7-methoxynaphth-1-yl)ethyl]-N'-methylurea

By replacing propyl isocyanate in Example 1 with methyl isocyanate, the title compound is obtained in the same manner.

Infra-red spectral characteristics: 3280 cm$^{-1}$: v NH (urea) 3060–2820 cm$^{-1}$: v CH (alkyls)

EXAMPLES 3 TO 9

By replacing propyl isocyanate in Example 1 with the corresponding isocyanates, the products of the following Examples are obtained in the same manner:

EXAMPLE 3

N-[2-(7-methoxynaphth-1-yl)ethyl]-N'-ethylurea

EXAMPLE 4

N-[2-(7-methoxynaphth-1-yl)ethyl]-N'-butylurea

Melting point: 106°–107° C.

EXAMPLE 5

N-[2-(7-methoxynaphth-1-yl)ethyl]-N'-benzylurea

EXAMPLE 6

N-[2-(7-methoxynaphth-1-yl)ethyl]-N'-(4-chlorophenylmethyl) urea

EXAMPLE 7

N-[2-(7-methoxynaphth-1-yl)ethyl]-N'-cyclopropylmethylurea

EXAMPLE 8

N-[2-(7-methoxynaphth-1-yl)ethyl]-N'-[bis(4-chlorophenyl)methyl]urea

EXAMPLE 9

N-[2-(7-methoxynaphth-1-yl)ethyl]-N'-cyclopropylurea

EXAMPLE 10

N-[2-(7-methoxynaphth-1-yl)ethyl]-N'-propylthiourea

Following the procedure of Example 1 but using propyl isothiocyanate, the title compound is obtained in the same manner.

Melting point: 95°–97° C. Infra-red spectral characteristics: 3240 cm$^{-1}$: v NH (thiourea) 3060–2800 cm$^{-1}$: v CH (alkyls)

EXAMPLES 11 TO 14

By replacing propyl isothiocyanate in Example 10 with the corresponding isothiocyanates, the compounds of the following Examples are obtained in the same manner:

EXAMPLE 11

N-[2-(7-methoxynaphth-1-yl)ethyl]-N'-methylthiourea

Melting point: 105°–107° C. Infra-red spectral characteristics: 3200 cm$^{-1}$: v NH (thiourea)

EXAMPLE 12

N-[2-(7-methoxynaphth-1-yl)ethyl]-N'-ethylthiourea

Melting point: 114°–115° C. Infra-red spectral characteristics: 3205 cm$^{-1}$: v NH (thiourea)

EXAMPLE 13

N-[2-(7-methoxynaphth-1-yl)ethyl]-N'-butylthiourea

Melting point: 65°–68° C. Infra-red spectral characteristics: 3240 cm$^{-1}$: v NH (thiourea)

EXAMPLE 14

N-[2-(7-methoxynaphth-1-yl)ethyl]-N'-isopropylthiourea

Infra-red spectral characteristics: 3230 cm$^{-1}$: v NH (thiourea)

EXAMPLE 15

N-methyl-N-[2-(7-methoxynaphth-1-yl)ethyl]-N'-propylurea

By replacing N-2-(7-methoxynaphth-1-yl)ethylamine in Example 1 with N-[2-(7-methoxynaphth-1-yl)ethyl]-N-methylamine, the title compound is obtained in the same manner.

Infra-red spectral characteristics: 3290 cm$^{-1}$: v NH (urea)

EXAMPLE 16

N-[2-(naphth-1-yl)ethyl]-N'-propylurea

By replacing 2-(7-methoxynaphth-1-yl)ethylamine in Example 1 with 2-(naphth-1-yl)ethylamine, the title compound is obtained in the same manner.

Infra-red spectral characteristics: 3280 cm$^{-1}$: ν NH (urea)

EXAMPLE 17

N-[2-(7-hydroxynaphth-1-yl)ethyl]-N'-propylurea

By replacing 2-(7-methoxynaphth-1-yl)ethylamine in Example 1 with 2-(7-hydroxynaphth-1-yl)ethylamine, the title compound is obtained in the same manner, after purification by chromatography over a silica column.

Infra-red spectral characteristics: 3280 cm$^1$: ν NH (urea) 3350 cm$^{-1}$: ν OH (phenol)

EXAMPLES 18 TO 21

Following the procedure of Example 1 but using the corresponding 1-(2-aminoethyl)-7-hydroxynaphthyl ether, the compounds of the following Examples are obtained in the same manner:

EXAMPLE 18

N-[2-(7-isopropyloxynaphth-1-yl)ethyl]-N'-propylurea

EXAMPLE 19

N-[2-(7-phenoxynaphth-1-yl)ethyl]-N'-propylurea

EXAMPLE 20

N-[2-(7-diphenylmethoxynapthth-1-yl)ethyl]-N'-propylurea

EXAMPLE 21

N-[2-(7-cyclohexyloxynaphth-1-yl)ethyl]-N'-propylurea

EXAMPLE 22

N-[2-(6-methoxynaphth-1-yl)ethyl]-N'-propylurea

By replacing 2-(7-methoxynaphth-1-yl)ethylamine in Example 1 with 2-(6-methoxynaphth-1-yl)ethylamine, the title compound is obtained in the same manner.

Infra-red spectral characteristics: 3300 cm$^{-1}$: ν NH (urea)

EXAMPLE 23

N-[2-(5-methoxynaphth-1-yl)ethyl]-N'-propylurea

By replacing 2-(7-methoxynaphth-1-yl)ethylamine in Example 1 with 2-(5-methoxynaphth-1-yl)ethylamine, the title compound is obtained in the same manner.

Infra-red spectral characteristics: 3300 cm$^{-1}$: ν NH (urea)

EXAMPLE 24

N-[2-(7-methoxynaphth-2-yl)ethyl]-N'-propylurea

By replacing 2-(7-methoxynaphth-1-yl)ethylamine in Example 1 with 2-(7-methoxynaphth-2-yl)ethylamine, the title compound is obtained in the same manner.

Infra-red spectral characteristics: 3290 cm$^{-1}$: ν NH (urea)

EXAMPLE 25

N-[2-(6-methoxynaphth-2-yl)ethyl]-N'-propylurea

By replacing 2-(7-methoxynaphth-1-yl)ethylamine in Example 1 with 2-(6-methoxynaphth-2-yl)ethylamine, the title compound is obtained in the same manner.

Infra-red spectral characteristics: 3300 cm$^{-1}$: ν NH (urea)

EXAMPLE 26

N-[2-(naphth-1-yl)ethyl]-N'-butylurea

By replacing propyl isocyanate in Example 16 with butyl isocyanate, the title compound is obtained in the same manner.

Infra-red spectral characteristics: 3275 cm$^{-1}$: ν NH (urea)

EXAMPLE 27

Test of Binding to Melatonin Receptors

The binding of the compounds of the invention to melatonin receptors was carried out according to conventional methods on receptors of the pars tuberalis of sheep (Journal of Neuroendocrinology (1989 ), 1, (1 ), 1–4).

The compounds of the invention bind in an extremely specific manner to the melatonin receptors with an affinity, for those exhibiting the most affinity, that is more than 100 times greater than that of melatonin itself. The best have a dissociation constant (Kd) of the order of $10^{-13}$ mol.l$^{-1}$, as compared with $6.3 \times 10^{-11}$ mol.l$^{-1}$ for melatonin itself.

EXAMPLE 28

Potentiation of Barbiturate-Induced Sleep

Mice (22–25 g) are injected with 50 mg.kg$^{-1}$ of pentobarbital by the intraperitoneal route. The time taken for sleep to occur and the duration of sleep are measured. Sleep is assumed to have occurred when the animals lose the righting reflex. The test compounds are administered by the intraperitoneal route 30 minutes prior to the injection of the barbiturate. The compounds of the invention increase the duration of sleep induced by pentobarbital.

EXAMPLE 29

Acute Toxicity Study

Acute toxicity was assessed after oral administration to groups of 8 mice (26±2 grams). The animals were observed at regular intervals during the first day and daily during the two weeks following the treatment. The LD$_{50}$, causing the death of 50% of the animals, was evaluated.

The LD$_{50}$ of the products tested is greater than 1500 mg.kg$^{-1}$ for the compounds of the invention which were studied, which indicates the low toxicity of the compounds of the invention.

EXAMPLE 30

Pharmaceutical Composition: Tablets

Tablets containing 10 mg of N-[2-(7-methoxynaphth-1-yl)ethyl]-N'-propylurea

| Formulation for 10,000 tablets: | |
| --- | --- |
| N-[2-(7-methoxynaphth-1-yl)ethyl]-N'-propylurea | 100 g |

-continued

| Formulation for 10,000 tablets: | |
|---|---|
| corn starch | 400 g |
| lactose | 360 g |
| magnesium stearate | 20 g |
| silica | 10 g |
| hydroxypropylcellulose | 10 g |

We claim:

1. A compound selected from those of formula I:

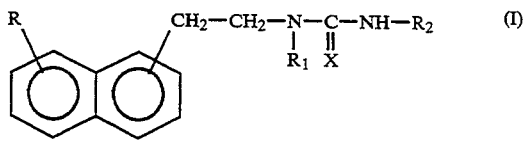

in which:
R represents hydrogen or a group $OR_3$ wherein $R_3$ represents straight-chained or branched alkyl having 1 to 6 carbon atoms inclusive;
$R_1$ represents hydrogen or straight-chained or branched alkyl having 1 to 6 carbon atoms inclusive;
X represents sulphur;
$R_2$ represents linear or branched lower alkyl having 1 to 6 carbon atoms inclusive, unsubstituted or optionally-substituted cycloalkyl having 3 to 8 carbon atoms, inclusive, $(C_3-C_8)$-cycloalkyl-$(C_1-C_6)$ alkyl,
addition salts thereof with a pharmaceutically-acceptable base, and
isomers, epimers and diastereoisomers thereof, wherein:
the term "substituted" associated with the expressions "cycloalkyl" and "cycloalkylalkyl" indicates that the cyclic system may be substituted by one or more groups selected from halogen, linear or branched lower alkyl having 1 to 6 carbon atoms inclusive, and linear or branched lower alkoxy having 1 to 6 carbon atoms inclusive.

2. A compound according to claim 1 selected from those in which R represents 7-methoxy and $R_1$ represents hydrogen, addition salts thereof with a pharmaceutically-acceptable base, and isomers, epimers and diastereoisomers thereof.

3. A compound of claim 1 which is N-[2-(7-methoxynaphth-1-yl)ethyl]-N'-propylthiourea.

4. A compound of claim 1 which is N-[2-(7-methoxynaphth-1-yl)ethyl]-N'-methylthiourea.

5. A compound of claim 1 which is N-[2-(7-methoxynaphth-1-yl)ethyl]-N'-ethylthiourea.

6. A compound of claim 1 which is N-[2-(7-methoxynaphth-1-yl)ethyl]-N'-butylthiourea.

7. A compound of claim 1 wherein $R_2$ represents unsubstituted or optionally-substituted cycloalkyl having 3 to 8 carbon atoms inclusive, or unsubstituted or optionally-substituted $(C_3-C_8)$-cycloalkyl-$(C_{1-6})$-alkyl.

8. A pharmaceutical composition useful in treating or in preventing a disorder of the melatoninergic system containing as active principle an effective amount of a compound selected from those of formula I

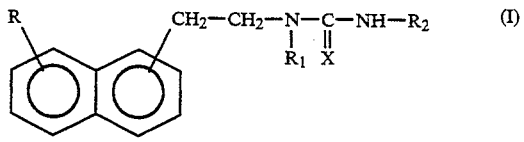

in which:
R represents hydrogen or a group $OR_3$ wherein $R_3$ represents straight-chained or branched alkyl having 1 to 6 carbon atoms inclusive,
$R_1$ represents hydrogen or straight-chained or branched alkyl having 1 to 6 carbon atoms inclusive;
X represents sulphur;
$R_2$ represents linear or branched lower alkyl having 1 to 6 carbon atoms inclusive, unsubstituted or optionally-substituted cycloalkyl having 3 to 8 carbon atoms inclusive, unsubstituted or optionally-substituted $(C_3-C_8)$-cycloalkyl-$(C_1-C_6)$-alkyl,
addition salts thereof with a pharmaceutically-acceptable base, and
isomers, epimers and diastereoisomers thereof, wherein
the term "substituted" associated with the expressions "cycloalkyl" and "cycloalkylalkyl" means that the cyclic system may be substituted by one or more groups selected from halogen, linear or branched lower alkyl having 1 to 6 carbon atoms inclusive, and linear or branched lower alkoxy having 1 to 6 carbon atoms inclusive, and
in combination with a pharmaceutically-acceptable excipient or vehicle.

9. A composition according to claim 8 wherein the compound is selected from those in which R represents hydrogen, or methoxy and $R_1$ represents hydrogen, addition salts thereof with a pharmaceutically-acceptable base, and isomers, epimers and diastereoisomers thereof.

10. A composition according to claim 8 wherein the compound is N-[2-(7-methoxynaphth-1-yl)ethyl]-N'-propylthiourea.

11. A composition according to claim 8 wherein the compound is N-[2-(7-methoxynaphth-1-yl)ethyl]-N'-methylthiourea.

12. A composition according to claim 8 wherein the compound is N-[2-(7-methoxynaphth-1-yl)ethyl]-N'-ethylthiourea.

13. A composition according to claim 8 wherein the compound is N-[2-(7-methoxynaphth-1-yl)ethyl]-N'-butylthiourea.

* * * * *

UNITED STATES PATENT AND TRADEMARK OFFICE
CERTIFICATE OF CORRECTION

PATENT NO. : 5,385,944
DATED : January 31, 1995
INVENTOR(S) : Daniel Lesieur, Said Yous, Patrick Depreux, Gèrard Adam, Pierre Renard, Bruno Pfeiffer, Bèatrice Guardiola-Lemaitre It is certified that error appears in the above-indentified patent and that said Letters Patent is hereby corrected as shown below:

```
Column  1, line  5; delete the word "invention"
Column  5, line 18; "-1-yl)" should read -- -2-yl) --
Column  5, line 26; "-1-yl)" should read -- -2-yl) --
Column  5, line 34; "0.011" should read -- 0.011 -- (no bold)
Column  5, line 45; start a new line with
     " 3040-2820 cm-¹:ν CH (alkyls)"
Column  5, line 46; start a new line with
     "1620-1600 cm-¹:ν CC (aromatic)"
Column  5, line 55; start a new line with
     "3060-2820 cm-¹:ν CH (alkyls)
Column  6, line 26; start a new line with
     "3060-2800 cm-¹:ν CH (alkyls)
```

Signed and Sealed this

Eighth Day of August, 1995

Attest:

Attesting Officer

BRUCE LEHMAN
Commissioner of Patents and Trademarks